US006247470B1

United States Patent
Ketchedjian

(10) Patent No.: US 6,247,470 B1
(45) Date of Patent: Jun. 19, 2001

(54) OXYGEN DELIVERY, OXYGEN DETECTION, CARBON DIOXIDE MONITORING (ODODAC) APPARATUS AND METHOD

(76) Inventor: Armen G. Ketchedjian, 656 Prospect St., New Haven, CT (US) 06511

( * ) Notice: Subject to any disclaimer, the term of this patent is extended or adjusted under 35 U.S.C. 154(b) by 0 days.

(21) Appl. No.: 09/349,287

(22) Filed: Jul. 7, 1999

(51) Int. Cl.[7] .................................................. A62B 29/00
(52) U.S. Cl. ............................. 128/200.28; 128/204.18; 128/201.24; 128/207.17; 128/207.18
(58) Field of Search .................. 128/200.28, 201.22, 128/201.18, 201.19, 200.27, 204.18, 207.17, 207.18, 201.24

(56) References Cited

U.S. PATENT DOCUMENTS

| | | | |
|---|---|---|---|
| 3,683,655 | * 8/1972 | White et al. ........................... 601/44 |
| 4,223,669 | * 9/1980 | Morledge ........................ 128/204.18 |
| 4,377,161 | * 3/1983 | Whitt ............................... 128/200.24 |
| 4,440,177 | 4/1984 | Anderson et al. . |
| 4,485,822 | * 12/1984 | O'Connor et al. .............. 128/207.17 |
| 4,509,551 | 4/1985 | Luper . |
| 4,593,688 | * 6/1986 | Payton ............................ 128/200.28 |
| 4,739,753 | * 4/1988 | Brehm ............................ 128/200.24 |
| 4,821,736 | 4/1989 | Watson . |
| 4,988,291 | * 1/1991 | Grummons ................................ 433/5 |
| 5,095,900 | 3/1992 | Fertig et al. . |
| 5,129,401 | 7/1992 | Corenman et al. . |
| 5,285,794 | 2/1994 | Lynch . |
| 5,293,875 | 3/1994 | Stone . |
| 5,335,656 | * 8/1994 | Bowe et al. ..................... 128/207.18 |
| 5,474,060 | 12/1995 | Evans . |
| 5,625,189 | 4/1997 | McCaul et al. . |
| 5,636,630 | 6/1997 | Miller et al. . |
| 5,697,363 | * 12/1997 | Hart ................................ 128/201.24 |
| 6,065,473 | * 5/2000 | McCombs et al. ............. 128/204.18 |

* cited by examiner

Primary Examiner—Aaron J. Lewis
Assistant Examiner—V. Srivastava
(74) Attorney, Agent, or Firm—DeLio & Peterson, LLC; Robert Curcio

(57) ABSTRACT

A respiratory device is disclosed that optimizes delivery of oxygen and detection of carbon dioxide to a user through the use of a flexible lever arm and mouthpiece which may be adjusted to deliver the oxygen toward the user's oral and nasal cavities, and detect carbon dioxide, exhaled by the user, from a separate orifice of the mouthpiece. The lever is supported by a rotatable adapter attached to a head mounted brace. The adapter can rotate through 180° for placement of the lever on either side of the user's head. The adapter is hinged to eliminate occluding and kinking during rotation. A hose having tubular members therein delivers the gases to and from the user. The hose traverses through the lever arm and adapter, terminating at the lever arm into the mouthpiece. The mouthpiece has a plurality of ports for fluid flow. The hose terminates at the other end in gas detection and delivery equipment. The hose may be segmented or one continuous piece.

36 Claims, 4 Drawing Sheets

OXYGEN DELIVERY, OXYGEN DETECTION, CARBON DIOXIDE MONITORING (ODODAC) APPARATUS AND METHOD

BACKGROUND OF THE INVENTION

1. Field of the Invention

The present invention is in the field of medical instruments. More specifically, it relates to an apparatus for delivery and collection of gases to and from a patient used during anesthesia.

2. Description of Related Art

Delivery of gases and monitoring of the patient's airway (capnography) is necessary during sedation anesthesia or analgesic anesthesia. Currently, for the majority of monitored anesthetic care (MAC), conscious sedation, standby, or any other procedure that involves the administration of sedative agents or anesthetics, nasal cannula are used as a method of supplemental oxygen delivery to the patient. The cannula are inserted into the nares, where the outflow of oxygen is inhaled by the patient, through the nose. This increases the margin of safety for oxygen delivery because the majority of sedatives are associated with a decrease in respiratory drive and can cause short or prolonged periods of apnea. In addition to sedatives that alter respiration activity, certain types of trauma and illnesses will also decrease the respiratory drive.

Many anesthesiologists have attempted to modify the design of the oxygen cannula, to not only deliver oxygen, but to also detect carbon dioxide, by inserting a variety of devices from angiocatheters to intravenous extension tubing to aid the sampling of carbon dioxide directly into the capnographic equipment. In one instance, an extra port in the nasal cannula was added in an attempt to improve carbon dioxide detection.

However, these devices work in a limited manner. They do not detect carbon dioxide sufficiently when the flow of oxygen is high. They also do not allow the sampling port (mouthpiece) to obtain an adequate amount of $CO_2$ for detection. The sampling port is under continuous suction; should it come against a structure or septum, it easily occludes or kinks. Additionally, not all patients breath through their nose; thus, negligible amounts of carbon dioxide would be detected if sampling at the level of the nares.

In U.S. Pat. No. 4,821,736, issued to Watson on Apr. 18, 1989, entitled, "HEAD-MOUNTED DEVICE FOR SUPPORTING BREATHING CIRCUIT TUBES AND SENSOR," a device for positioning the carbon dioxide sensor and breathing tubes adjacent the centerline of the forehead and above the head is taught. This system includes as its principal elements, in serial arrangement, an endotracheal tube, a sensor, a pair of breathing circuit tubes, and a breathing machine. The distal end of the endotracheal tube has a portion which is inserted in one of the patient's nostrils. The supporting device requires a cushion, a rigid plate, a headband, and two mushroom connecting members. The cushion is positioned lengthwise across the forehead with an inner surface placed on the forehead and on opposing outer surfaces. Central to this invention, the sensor and tubes are held securely along the patient's forehead without pulling on or otherwise irritating any part of the patient.

U.S. Pat. No. 5,046,491, issued to Derrick on Sep. 10, 1991, entitled, "APPARATUS AND METHOD FOR RESPIRED GAS COLLECTION AND ANALYSIS," teaches a nasal gas cannula and an oral gas capture member constructed and arranged to avoid or minimize contact with the patient's mouth and other facial surfaces. This patent emphasizes maintaining a substantially fluid tight seal between a mask and surfaces of the patient's face. Central to this invention is an oral gas hood (mask) with an approximate ellipsoidal peripheral configuration with a major axis and a minor axis, each of which is respectively larger than the length and height of the patient's mouth.

U.S. Pat. No. 5,636,630, issued to Miller, et al., on Jun. 10, 1997, entitled, "RESPIRATORY DEVICE AND METHOD THEREFOR," teaches of a conduit passing above the patient's left and right ears, coupled to the patient's nostrils for supplying a fluid to the patient, a coupling portion contacting a back portion of the patient's head, and a cavity through which the conduit portion passes for securely coupling the conduit portion around the patient's head. The coupling means is located below the patient's left and right ears, on the backside of the patient's head. Unlike the other cited prior art, Miller's invention is restricted to only one conduit line, presumably for detection or delivery of gas, but not both.

Watson, Derrick, and Miller all use head-mounted devices. However, they do not utilize a flexible lever or arm rotatably attached to a headset, for positioning the conduit tubular members close to the patient's orifices. In Watson, a headband is necessary to secure the conduit tubes to the patient's forehead. Similarly, in Derrick, an oral gas hood is secured to the patient's skin about the mouth and nose, with conduit tubing traversing about and around the patient's head. Additionally, the mounting of the conduit assembly in a headset fashion has not been suggested or disclosed in any of the cited prior art. Furthermore, in other gas detection and delivery designs, the nosepiece is intrusively mounted to the nasal passages and then expanded in order to create a compression fit that precludes air leakage.

The problems of occluding, kinking, maintaining a seal about the patient's orifices for continuous suction, and detecting carbon dioxide when the flow of oxygen is high, remain in various prior art designs.

Bearing in mind the problems and deficiencies of the prior art, it is therefore an object of the present invention to provide an apparatus and method for mounting the mouthpiece of an oxygen delivery and carbon dioxide detection system nonintrusively to the patient's orifices.

It is another object of the present invention to provide an apparatus for attaching conduit tubes close to, but not touching, the patient's orifices.

A further object of the invention is to provide an apparatus and method for delivering oxygen and detecting carbon dioxide in a respiratory device that is not prone to occlude or kink.

It is yet another object of the present invention to provide an apparatus and method for gas delivery, detection, and monitoring that does not decrease the respiratory drive during operation.

A further object of the present invention is to provide an apparatus and method for gas delivery, detection, and monitoring that is adjustable for attachment on either side of the patient while providing minimum contact with the patient.

Still other advantages of the invention will in part be obvious and will in part be apparent from the specification.

SUMMARY OF THE INVENTION

The above and other advantages, which will be apparent to one of skill in the art, are achieved in the present invention which is directed to, in a first aspect, a respiratory device comprising: a head support for fitting a user's head, from one ear region of the user, over the top of the user's head, to the user's other ear region; and, a lever arm having a first end connected to the head support near the one ear region, and a second end extending in a cantilever fashion away from the first end, the second end in vicinity of but spaced from the user's nose and mouth region.

The second end is adapted to deliver gas to the user and receive exhaled gas from the user. The lever arm is adapted to deliver oxygen to the user and receive carbon dioxide from the user, and is adapted to rotate about the head support.

The respiratory device further comprises: an adapter, connected to the head support at the one ear region, and providing attachment for the lever arm; and, a pad, connected to the head support at the other ear region.

In a second aspect, the present invention is directed to a respiratory device comprising: a lever arm having first and second ends; a conduit having first and second ends, the conduit traversing through and supported by the arm; a connector supporting the first end of the arm, the connector having a base portion and an adapter portion, the conduit traversing through the adapter portion; a headset having first and second ends, adapted to fit over the top of a user's head, the first end of the headset adapted to hold and secure the adapter, the second end of the headset adapted to hold and secure a pad; and, a mouthpiece connected to the second end of the arm and terminating the first end of the conduit.

This device further comprising gas monitoring and detection equipment attached to the second end of the conduit. The lever arm is rigidly flexible, capable of moving and maintaining a plurality of set positions. A soft material is attached to the base portion of the connector and to the pad. The arm is adapted to allow the mouthpiece to be detached, and the connector is adapted to allow the conduit and the base to be detached.

The mouthpiece non-intrusively covers the user's oral and nasal orifices. It comprises a plurality of holes for delivery of the oxygen to the user, and for delivery of carbon dioxide from the user. The adapter is rotatable with respect to the base, and can be rotated through 180° with respect to the base.

The conduit comprises at least two tubular members adapted to deliver fluid to and from the user. The base and the pad are adapted to allow the soft material to be detached. The plurality of holes are situated such that the holes for oxygen delivery are above the holes for carbon dioxide delivery, the oxygen delivery holes being closer to the user's nasal cavity.

The conduit further comprises a hose having a first end and a second end, the hose encompassing the tubular members. The hose may be segmented, having a first segment traversing through the arm and attaching to the adapter, and a second segment extending from the adapter, or, the hose may be one continuous piece with the first end terminating at the mouthpiece and the second end terminating at fluid delivery and detection equipment.

In a third aspect, the present invention is directed to a gas delivery and detection system comprising: a head mounted brace having a first and second end, a rotatable connector attached to the first end of the head mounted brace; a plurality of tubular members; the connector having a base and an adapter, the adapter being rotatable with respect to the base, and having the plurality of tubular members traversing therethrough; at least some of the tubular members connected to a gas delivery system, and the remaining of the tubular members connected to a gas detection system; and, a flexible arm attached to the adapter and supporting the tubular members, the arm terminating the tubular members at a mouthpiece; the mouthpiece having plurality of ports for gas delivery and gas detection.

The adapter may further comprise a hinge, the hinge adapted to allow rotation of the adapter without occluding or kinking the tubular means. The flexible arm is adapted to be positioned and maintained such that the mouthpiece is situated about, but not in contact with, a user's oral and nasal orifices.

The present invention is directed to, in a fourth aspect, a method for gas detection and delivery comprising the steps of: a) providing an apparatus including:

1) a head support for fitting a user's head, from one ear region of the user, over the top of the user's head, to the user's other ear region; and, 2) a lever arm having a first end connected to the head support near the one ear region, and a second end extending in a cantilever fashion away from the first end, the second end in vicinity of but spaced from the user's nose and mouth region; b) placing the apparatus on the user's head such that the head support traverses over the top of the user's head; c) adjusting the lever arm second end in the vicinity of the user's oral and nasal orifices; and, d) supplying oxygen to the user through the lever arm second end, and receiving carbon dioxide exhaled by the user through the lever arm second end.

Adjusting the lever arm, may comprise rotating the lever arm with respect to the head support.

In a fifth aspect, the present invention is directed to a method for gas detection and delivery comprising the steps of: a) providing a head mounted brace having a first end and a second end, the brace second end supporting a rotatable adapter and base; b) applying the head mounted brace about a user's head; c) positioning the brace first and second ends such that the first end is near the user's ear, and the second end is near the user's opposite ear; d) positioning a lever arm and mouthpiece near the user's oral and nasal orifices, keeping the mouthpiece out of contact with the user; e) connecting conduits traversing through the adapter to gas delivery and gas detection equipment; f) delivering gas to the user; and, g) detecting gas and monitoring gas exhaled by the user.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE PREFERRED EMBODIMENT(S)

Figure 1:
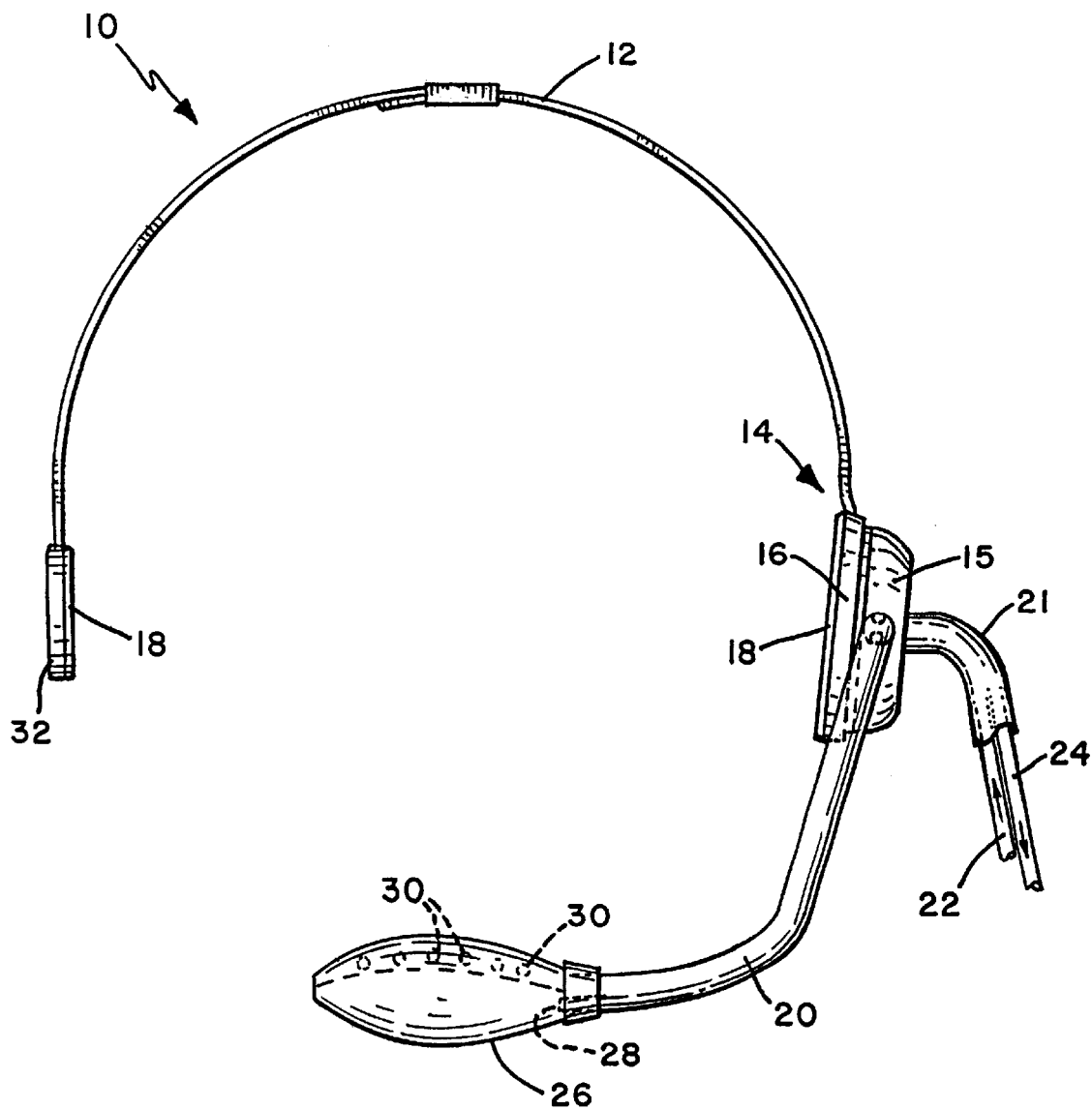
FIG. 1 depicts the elements of the ODODAC apparatus.

In describing the preferred embodiment of the present invention, reference will be made herein to FIGS. 1–4 of the drawings in which like numerals refer to like features of the invention. Features of the invention are not necessarily shown to scale in the drawings.

This invention is an apparatus for delivering oxygen to a person and detecting oxygen and carbon dioxide expelled from the person. It may be used by the person anywhere, but is particularly useful in the operating room or any other facility equipped for major or minor surgical procedures. In the prior art designs the $O_2$ cannula has not been the most optimum design to deliver oxygen to patients who are having nasal surgery, it often interferes with the surgical preparation and exposure, and needs to be taped away, below the mouth. This decreases the effectiveness of the $O_2$ delivery and $CO_2$ detection.

The oxygen delivery, oxygen detection, and carbon dioxide (ODODAC) monitoring apparatus optimizes delivery, detection, and monitoring through the use of a flexible lever or arm attached to a headset or head mounted brace. The apparatus is adapted to be adjusted to non-intrusively deliver the oxygen optimally toward the oral and nasal cavities and detect carbon dioxide from a separate orifice within a mouthpiece attached to the flexible arm.

The arm extends from an earpiece connector adapter attached to a headset or head mounted brace. The adapter incorporates oxygen delivery tubular members and the gas detection tubular members in separate tubes within a flexible hose. The headset portion secures the earpiece connector and flexible arm to the patient's head. The arm and mouthpiece may be adjusted for desired location in the vicinity of the person's oral and nasal cavities.

FIG. 1 depicts the elements of the ODODAC apparatus 10. An adjustable headset 12 is attached at one end to an earpiece connector 14 encompassing an adapter 15. The adapter 15 houses a conduit of at least two tubular members; an inhale or delivery tube 22 and an exhale or detection tube 24. The other end of headset 12 is attached to a securing pad 32. The earpiece connector 14 includes a base 16, attached to adapter 15, and lined with soft material 18 to cushion the connector when pressed against the patient's head. Similarly, securing pad 32 is also lined with the soft material 18 for a comfortable fitting of the headset on a patient's head. The soft material 18, base 16, and securing pad 32 may all be replaceable and disposable items to ensure sanitary conditions after each use.

The adapter 15 is capable of at least 180° rotation with respect to the base 16. This allows the headset 10 to be completely reversed and used on either side of the patient's head.

A flexible arm 20 carries the tubular members (inhale tube 22 and exhale tube 24) to the patient's orifices, terminating at a mouthpiece 26. The arm is rigidly flexible; capable of being moved and set in a plurality of positions. The material for the earpiece connector, adapter, headset, and mouthpiece may be any light weight, durable material that is not reactive to the gases delivered to or exhaled by the patient. Preferably, this material is a light weight plastic. The arm 20 is preferably adjusted to deliver the oxygen optimally toward the oral and nasal cavities. The mouthpiece is non-intrusive and does not require a seal to the patient. The mouthpiece is also detachable and disposable, capable of being removed and replaced after each use. It has a plurality of ports for oxygen delivery 30 and carbon dioxide detection 28. The oxygen delivery ports 30 are connected to the inhale tube 22, and the carbon dioxide ports 28 are connected to the exhale tube 24. Through these tubular members gases, such as oxygen, can be delivered through one orifice 30 while gases, such as carbon dioxide, may be monitored and detected from a separate orifice 28. Although the ODODAC apparatus has been designed preferably for oxygen delivery and carbon dioxide detection, other fluids that are non-destructive or non-degrading to the tubular member material may also be delivered and detected.

The arm 20 extends from adapter 15. The gas delivery and detection is performed through the separate tubes 22, 24 within the arm 20. After the tubular members traverse the adapter, a hose segment 21, extending from the opposite side of adapter 15, carries the tubular members to a control/monitor station for the delivery of the oxygen and the detection of carbon dioxide. This hose segment may be part of the same hose segment within arm 20, or may be separately attached to the tubular members within the arm, in the adapter. The hose, represented by the hose segment within arm 20, and hose segment 21, extending from the adapter, may be detachable for cleaning or disposing.

Figure 2A:
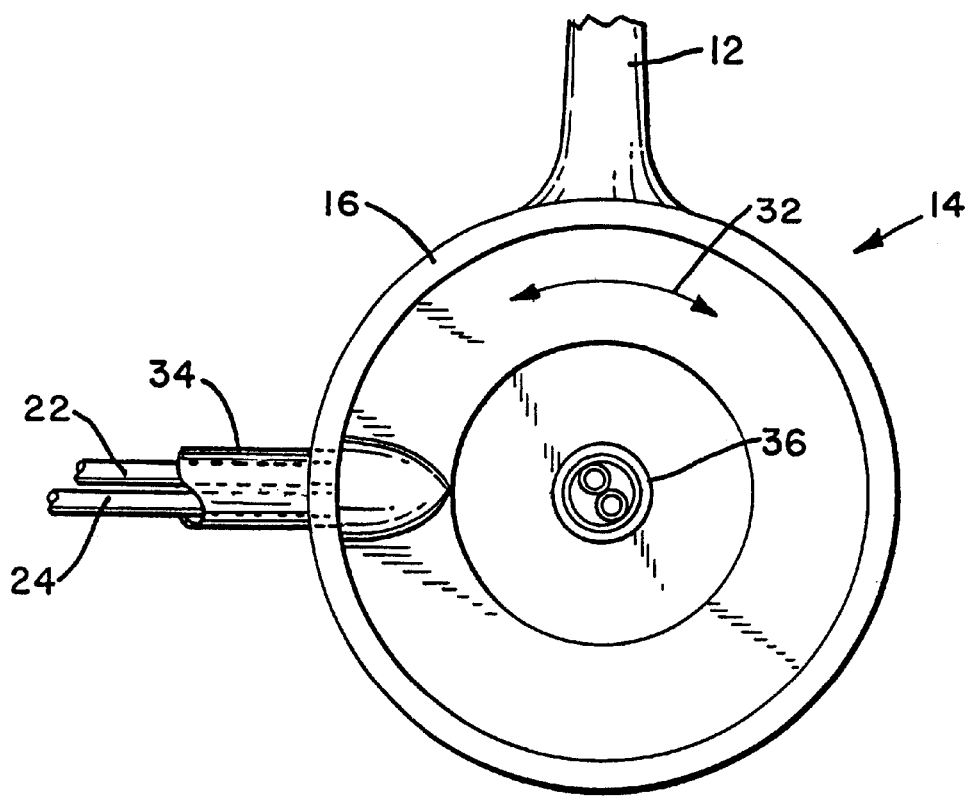
FIG. 2A is a bottom cross-sectional view of the earpiece connector.

FIG. 2A is a bottom cross-sectional view of the ear piece connector 14. Arrow 32 indicates the possible directions of the adapter rotation. By rotating through 180°, the adapter 15 can be situated to allow the headset for placement on the patient's right or left side. This is accomplished without occluding or introducing kinks in the air tubes. An outer cover 34 binds and encloses the inhale and exhale tubular members 22, 24 such that one hose segment leads to the mouthpiece 26.

Figure 2B:
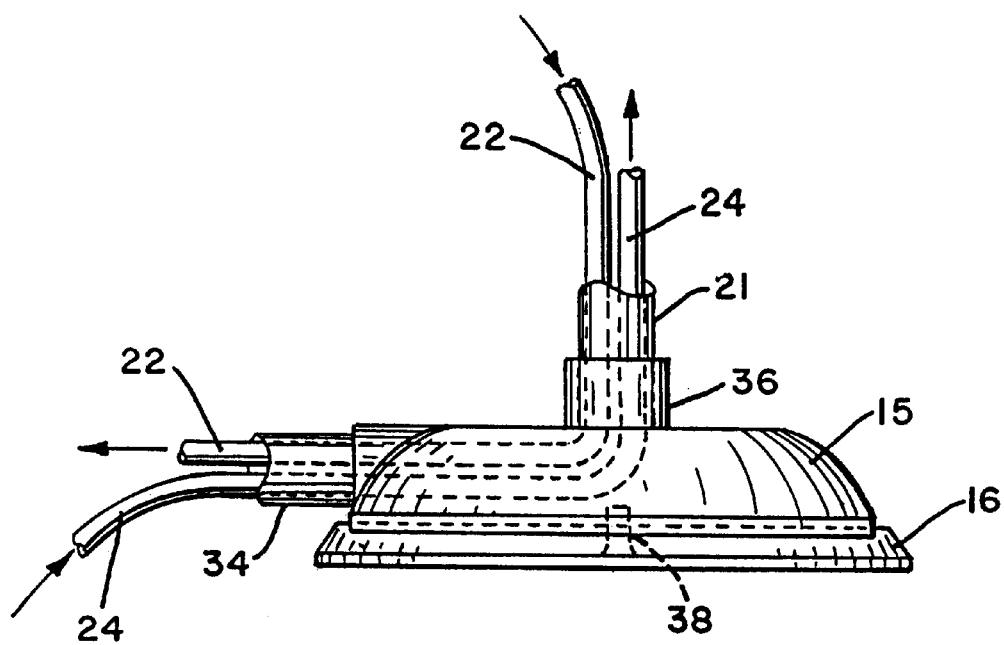
FIG. 2B represents a side cross-sectional view through the earpiece connector, depicting the tubular member paths through the adapter.

Aperture 36 provides a port through the center of adapter 15, on the side opposite the adapter base 16, for the tubes to traverse through hose 21 to and from a control center (not shown) housing gas delivery, detection, and monitoring equipment. FIG. 2B represents a side cross-sectional view through the earpiece connector, depicting the tubular member paths from the side of the adapter, through its center, and through aperture 36. A hinge 38 is used to allow for rotational movement without occluding or kinking the tubes within the earpiece connector.

Figure 3A:
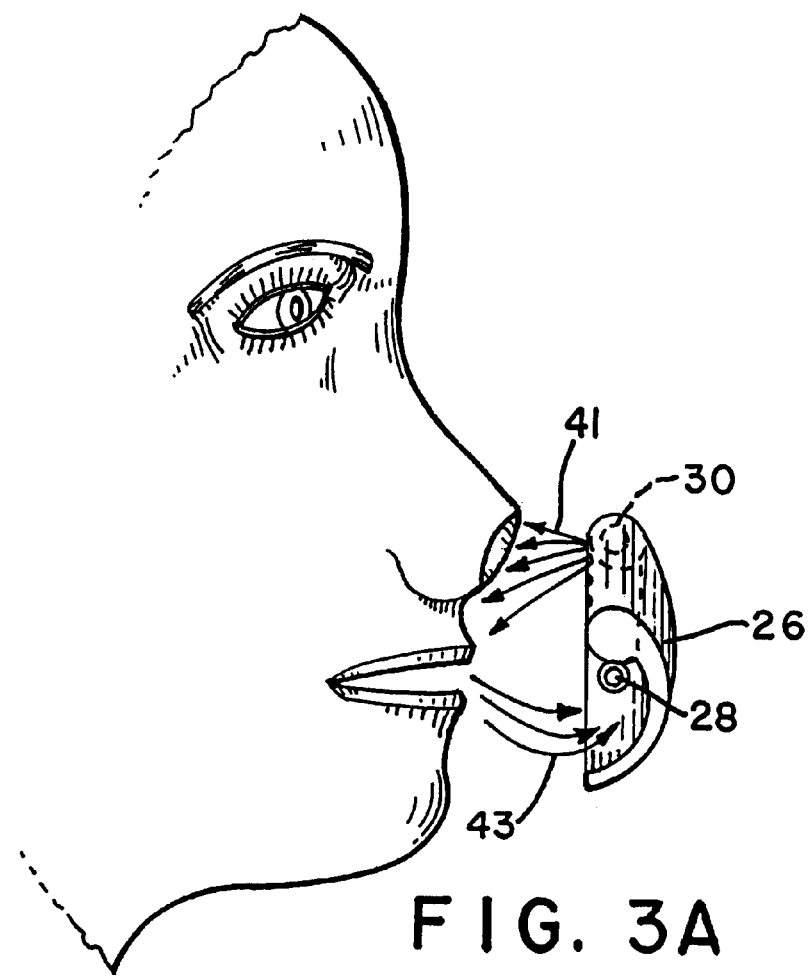
FIG. 3A is a cross-sectional view of mouthpiece.

FIG. 3A is a cross-sectional view of mouthpiece 26, depicting the location of the mouthpiece about the patient's orifices. Importantly, the mouthpiece does not touch the patient. The oxygen port 30, used to deliver $O_2$ to the patient, is located above the carbon dioxide port 28. The arrows 41, 43 indicate the direction of gas flow. As shown, carbon dioxide port 28 is nearer to the patient's mouth for receiving exhaled $CO_2$ from the patient.

Figure 3B:
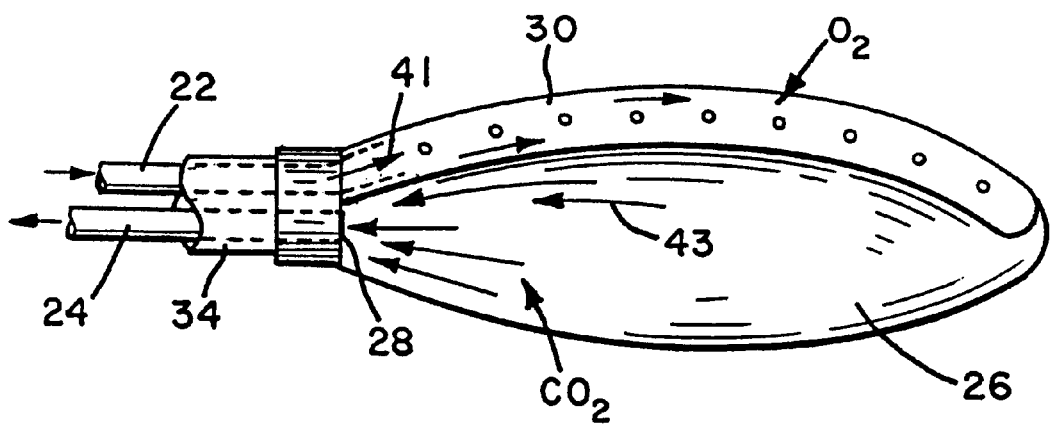
FIG. 3B represents the mouthpiece as seen from the side facing the patient.

FIG. 3B represents the mouthpiece as seen from the side facing the patient. The larger carbon dioxide port 28 collects a substantial amount of exhaled air, while the narrower oxygen port delivers the necessary $O_2$ to the patient. The mouthpiece 26 may be curved or shaped to cover the mouth and nasal cavities respectively without making contact thereto.

Figure 4:
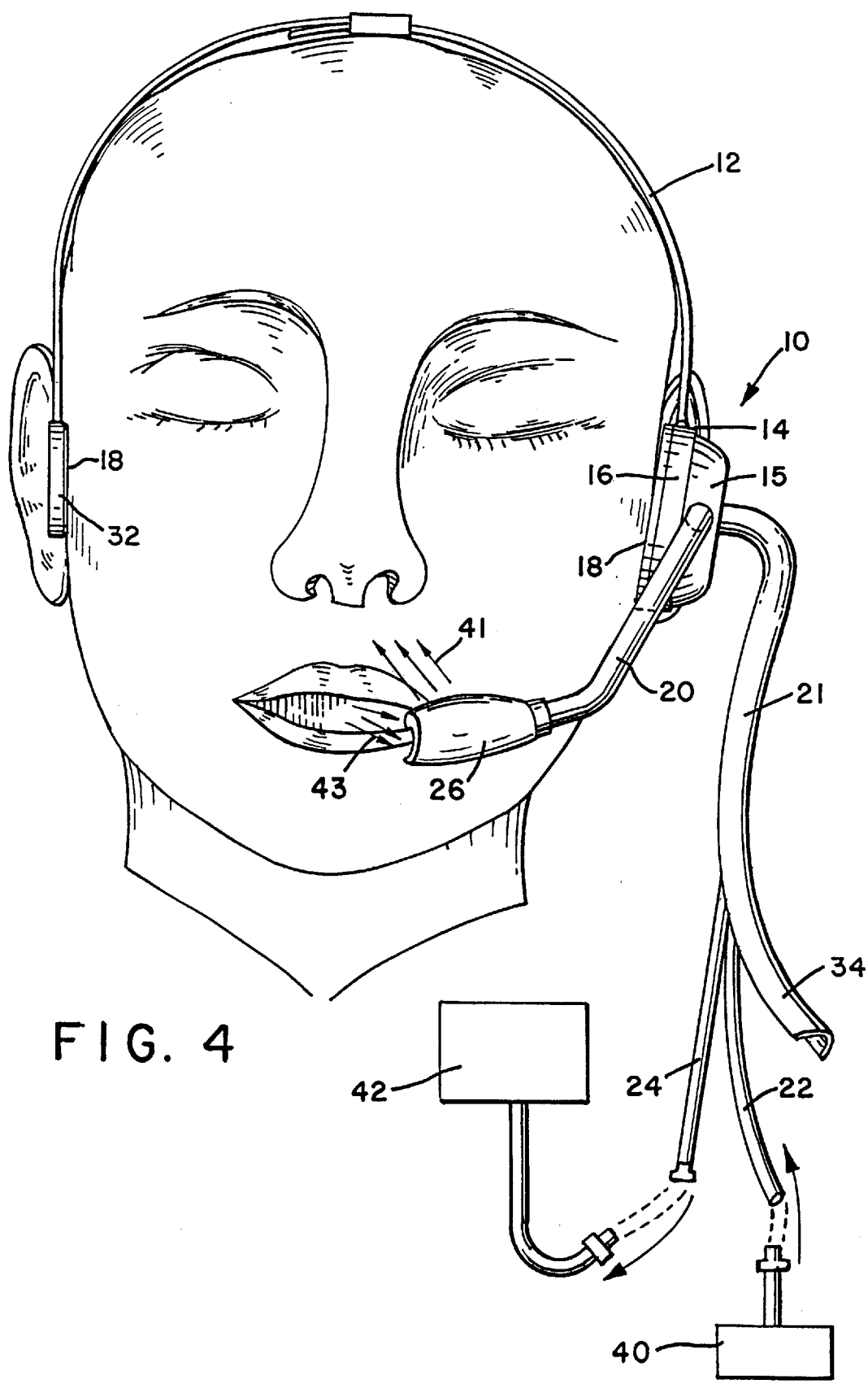
FIG. 4 depicts the placement of the ODODAC apparatus about the patient's head.

FIG. 4 depicts the placement of the apparatus 10 on a patient's head. The headset 12 is placed around the patient's head such that earpiece connector 14 and securing pad 32 are opposite each other and relatively close to or partially in contact with each ear of the patient. Arm 20 carries the gas delivery and gas detection hoses 22, 24 to the mouthpiece 26, holding the mouthpiece close to, but not touching, the patient's mouth and nasal cavities.

Hose 21 attaches to earpiece connector 14 through aperture 36, bringing the inhale and exhale tubular members to an oxygen source 40 and a carbon dioxide monitoring station 42, respectively.

The apparatus of the present invention provides for a unique method of application. First, the head mounted brace is placed over the user's head in a headset fashion. The brace is positioned so that pad end is in the vicinity of the user's ear, and the earpiece connector end is in the vicinity of the user's opposite ear. The lever arm is then positioned to place the mouthpiece close to the user's oral and nasal cavities. Since the lever arm is flexible, it is bent into position and remains stationary until further movement is attempted. The conduit extending from the adapter is then connected to gas delivery and detection equipment. Since the adapter on the head mounted brace is rotatable, the head mounted brace may be reversed, and the lever arm positioned on either side of the user's face.

This respiratory device provides a non-intrusive way to deliver and detect fluids (gases) to and from a user. It optimizes the delivery of oxygen and the detection of carbon dioxide during surgical procedures, while reducing or eliminating occluding and kinking. It also provides a means for optimally detecting carbon dioxide during times of high oxygen delivery.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A respiratory device comprising:
   a head support for fitting on a user's head, from one ear region of a user, over the top of a user's head, to a user's other ear region;
   a lever arm having a first end connected to the head support near a one ear region, and a second end extending in a cantilever fashion away from the first end, the second end spaced away from said user's nose and mouth region; and,
   a mouthpiece connected to the second end of the arm comprising a first plurality of holes for delivery of a first fluid to a user and a second plurality of holes for receiving a second fluid from said user without covering said user's nose, the first plurality of holes situated near said user's nose and the second plurality of holes situated near said user's mouth.

2. The respiratory device of claim 1 wherein the second end is adapted to deliver gas to a user and receive exhaled gas from a user.

3. The respiratory device of claim 1 wherein the lever arm is adapted to deliver oxygen to a user and receive carbon dioxide from a user.

4. The respiratory device of claim 1 wherein the lever arm is adapted to rotate about the head support.

5. The respiratory device of claim 1 further comprising:
   an adapter, connected to the head support at the one ear region, and providing attachment for the lever arm; and,
   a pad, connected to the head support at the other ear region.

6. A respiratory device comprising:
   a lever arm having first and second ends;
   a conduit having first and second ends, the conduit traversing through and supported by the arm;
   a connector supporting the first end of the arm, the connector having a base portion and an adapter portion, the conduit traversing through the adapter portion;
   a headset having first and second ends, adapted to fit over the top of a user's head, the first end of the headset adapted to hold and secure the adapter, the adapter rotatable to 180° with respect to the base, the second end of the headset adapted to hold and secure a pad; and,
   a mouthpiece connected to the second end of the arm and terminating the first end of the conduit comprising a first plurality of holes for delivery of a first fluid to a user and a second plurality of holes for receiving a second fluid from said user, the mouthpiece adjacent to but not covering said user's nose, the first plurality of holes situated near said user's nose and the second plurality of holes situated near said user's mouth.

7. The device of claim 6 further comprising gas monitoring and detection equipment attached to the second end of the conduit.

8. The device of claim 6 wherein the lever arm is rigidly flexible, capable of moving and maintaining a plurality of set positions.

9. The device of claim 6 wherein a soft material is attached to the base portion of the connector and to the pad.

10. The device of claim 6 wherein the arm is adapted to allow the mouthpiece to be detached.

11. The device of claim 6 wherein the connector is adapted to allow the conduit and the base to be detached.

12. The device of claim 6 wherein the mouthpiece non-intrusively covers the user's oral and nasal orifices.

13. The device of claim 6 further comprises a plurality of holes for delivery of oxygen to a user, and for delivery of carbon dioxide from said user to a detection equipment.

14. The device of claim 6 wherein the adapter is rotatable with respect to the base.

15. The device of claim 6 wherein the conduit comprises at least two tubular members adapted to deliver fluid to and from a user.

16. The device of claim 9 wherein the base and the pad are adapted to allow the soft material to be detached.

17. The device of claim 13 wherein the plurality of holes are situated such that the holes for oxygen delivery are above the holes for carbon dioxide delivery, the oxygen delivery holes being closer to a user's nasal cavity.

18. The device of claim 15 wherein the conduit further comprises a hose having a first end and a second end, the hose encompassing the tubular members.

19. The device of claim 18 wherein the hose is segmented, having a first segment traversing through the arm and attaching to the adapter, and a second segment extending from the adapter.

20. The device of claim 18 wherein the hose is one continuous piece with the first end terminating at the mouthpiece and the second end terminating at fluid delivery and detection equipment.

21. The device of claim 15 wherein the conduit is adapted to deliver oxygen to a user and carbon dioxide from said user.

22. The device of claim 15 wherein the hose second end directs the conduit to a fluid delivery system, and a fluid monitoring and detection system.

23. The device of claim 22 wherein the fluid delivery system is an oxygen delivery system, and the fluid monitoring and detection system is a carbon dioxide monitor and detection system.

24. A gas delivery and detection system comprising:

a head mounted brace having a first and second end, a rotatable connector attached to the first end of the head mounted brace;

a plurality of tubular members;

the connector having a base and an adapter, the adapter being rotatable to 180° with respect to the base, and having the plurality of tubular members traversing therethrough;

at least some of the tubular members connected to a gas delivery system, and the remaining of the tubular members connected to a gas detection system; and, a flexible arm attached to the adapter and supporting the tubular members, the arm terminating the tubular members at a mouthpiece;

the mouthpiece having plurality of ports for gas delivery and gas detection comprising a first plurality of ports for delivery of a first fluid to a user and a second plurality of ports for receiving a second fluid from said user, the mouthpiece adjacent to but not covering said user's nose, the first plurality of ports situated near said user's nose and the second plurality of ports situated near said user's mouth.

25. The gas delivery and detection system of claim 24 wherein the adapter further comprises a hinge, the hinge adapted to allow rotation of the adapter without occluding or kinking the tubular means.

26. The gas delivery and detection system of claim 24 further comprising a securing pad attached to the second end of the head mounted brace.

27. The gas delivery and detection system of claim 26 wherein the base and the securing pad are covered with a soft material for placement against said user.

28. The gas delivery and detection system of claim 24 wherein the mouthpiece comprises an upper portion for gas delivery and a lower portion for gas detection.

29. The gas delivery and detection system of claim 24 wherein the tubular members are encased together within a hose.

30. The gas delivery and detection system of claim 24 wherein the flexible arm is adapted to be positioned and maintained such that the mouthpiece is situated about, but not in contact with, a user's oral and nasal orifices.

31. A method for gas detection and delivery comprising the steps of:
   a) providing an apparatus including:
      1) a head support for fitting on a user's head, from one ear region of said user, over the top of said user's head, to said user's other ear region; and,
      2) a lever arm capable of 180° rotation, having a first end connected to the head support near said one ear region, and a second end extending in a cantilever fashion away from the first end, the second end spaced away from said user's nose and mouth region;
   b) placing the apparatus on a user's head such that the head support traverses over the top of said user's head;
   c) adjusting the lever arm second end in the vicinity of said user's oral and nasal orifices;
   d) adjusting a mouthpiece comprising a first plurality of ports for delivery of a first fluid to said user and a second plurality of ports for receiving a second fluid from said user, the mouthpiece adjacent to but not covering said user's nose, such that the first plurality of ports are situated near said user's nose and the second plurality of ports are situated near said user's mouth; and,
   e) supplying oxygen to said user through the lever arm second end, and receiving carbon dioxide exhaled by said user through the lever arm second end.

32. The method of claim 31 wherein the step of adjusting the lever arm, comprises rotating the lever arm with respect to the head support.

33. A method for gas detection and delivery comprising the steps of:
   a) providing a head mounted brace having a first end and a second end, the brace second end supporting a rotatable adapter and base;
   b) applying the head mounted brace about a user's head;
   c) positioning the brace first and second ends such that the first end is near a user's ear, and the second end is near said user's opposite ear;
   d) positioning a lever arm and mouthpiece near said user's oral and nasal orifices, keeping the mouthpiece out of contact with said user by adjusting the mouthpiece comprising a first plurality of ports for delivery of a first fluid to said user and a second plurality of ports for receiving a second fluid from said user, adjacent to but not covering said user's nose, such that the first plurality of ports are situated near said user's nose and the second plurality of ports are situated near said user's mouth;
   e) connecting conduits traversing through the adapter to gas delivery and gas detection equipment;
   f) delivering gas to said user; and,
   g) detecting gas and monitoring gas exhaled by said user.

34. The method of claim 33 wherein the step of delivering gas to a user, comprises delivering oxygen to a user.

35. The method of claim 33 wherein the step of detecting and monitoring gas, comprises detecting and monitoring carbon dioxide.

36. The method of claim 33 wherein the step of positioning the lever arm and mouthpiece, further comprises rotating the lever arm about the adapter.

* * * * *